United States Patent [19]
Lott

[11] Patent Number: 5,636,918
[45] Date of Patent: Jun. 10, 1997

[54] PRECISION SIGHTING INSTRUMENT FOR VIEWING OBSTRUCTED AREAS

[76] Inventor: Jeffrey M. Lott, 2161 Clematis St., San Diego, Calif. 92105

[21] Appl. No.: 697,856

[22] Filed: Aug. 30, 1996

[51] Int. Cl.$^6$ ..................................................... F21V 33/00
[52] U.S. Cl. ............................ 362/139; 362/142; 362/208
[58] Field of Search ................................. 362/139, 135, 362/138, 142, 144, 208

[56] References Cited

U.S. PATENT DOCUMENTS

| | | | |
|---|---|---|---|
| 1,462,398 | 7/1923 | Van Nostrand | 362/139 |
| 1,656,754 | 1/1928 | Norris . | |
| 1,750,194 | 3/1930 | Rydman . | |
| 2,107,791 | 2/1938 | Henning . | |
| 2,222,879 | 11/1940 | Porter . | |
| 2,652,479 | 9/1953 | Wilson | 362/138 |
| 4,907,135 | 3/1990 | Torrson et al. | 362/109 |
| 5,428,484 | 6/1995 | Baker | 359/872 |

*Primary Examiner*—Stephen F. Husar
*Attorney, Agent, or Firm*—Patrick H. Higgins, Esq.

[57] ABSTRACT

A precision sighting device is provided for viewing dark recesses as well as obstructed areas in general which are difficult to see with the naked eye comprising a longitudinally extendable/retractable rigid rodlike member, a focusable light source mounted at one end of the rodlike member, longitudinally parallel and adjacent to the rodlike member by at least one holding bracket such that light may be emitted from the focusable light source and directed lengthwise and parallel to the rodlike member toward an opposite end of the rodlike member, a tandem ball joint at said opposite end of the rodlike member formed in part by a first ball integral to said opposite end of the rodlike member, and a mirror pivotally connected by a flange extending from a peripheral portion of the mirror, to a second ball of said tandem ball joint—such that light emitted from the focusable light source may form a focal point or area on the center of the mirror at an exponential number of positions of the mirror with respect to a focal length of light emitted from the focusable light source. An object of the invention is to provide a focusable high intensity light source integral to a compact structural design to consistently provide for optical convergence of light at a center point of an integral mirror at many different focal lengths from the light source and angular positions of the mirror with respect to the integral light source. Another object of the invention is to provide an instrument which is especially suited for precision in aiming light and illuminating details very brightly for accurate and clear viewing while greatly reducing light reflected from the background of the area surrounding the mirror thereby providing much improved visual contrast.

20 Claims, 2 Drawing Sheets

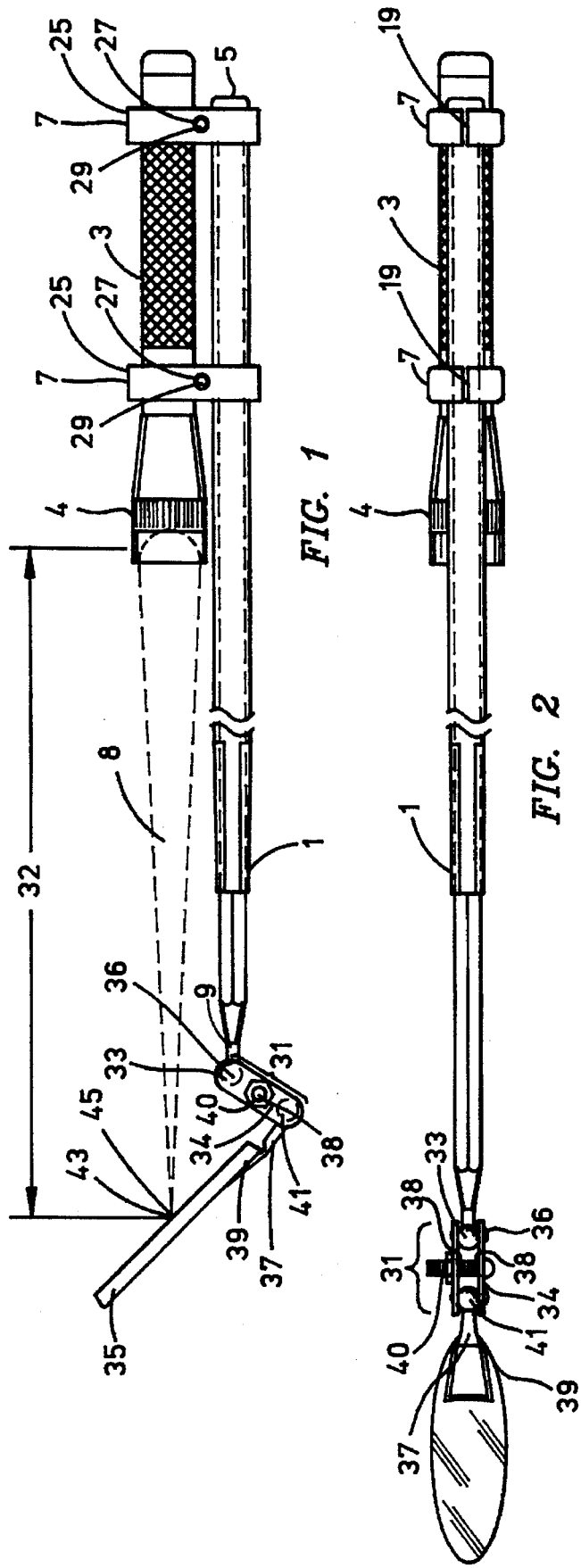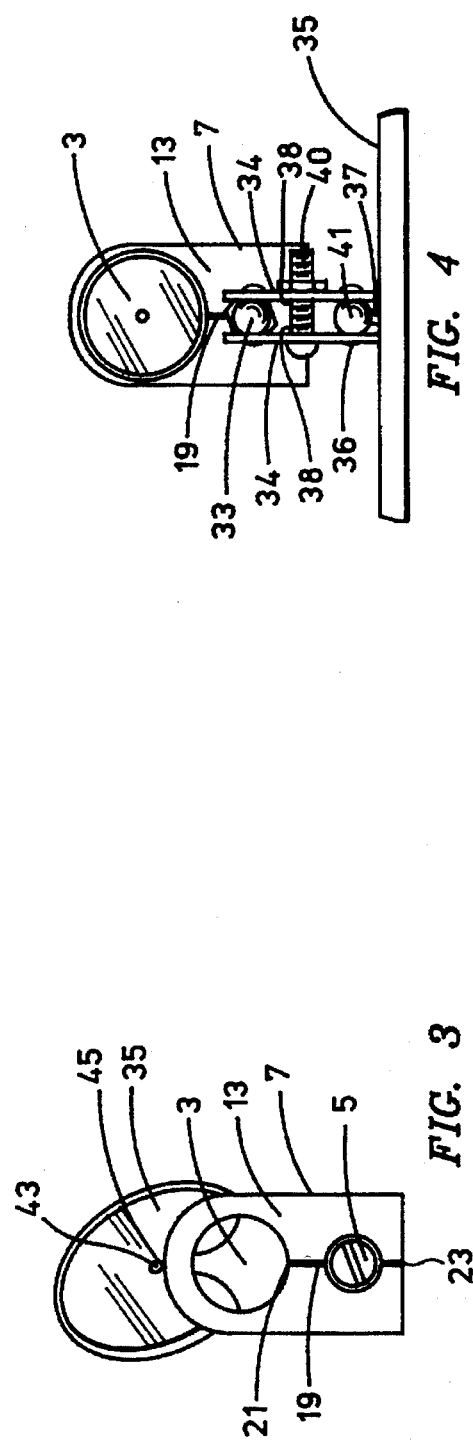

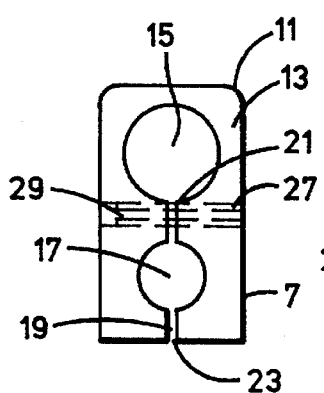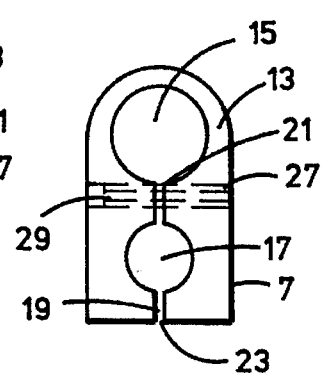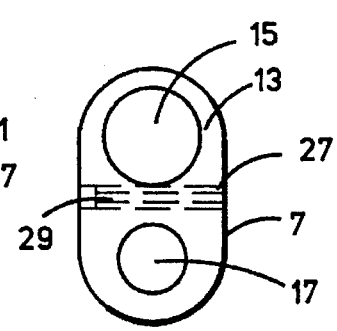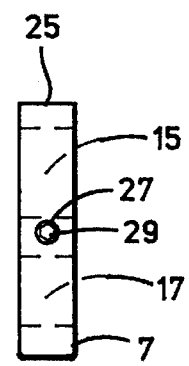
FIG. 5  FIG. 6  FIG. 7  FIG. 8
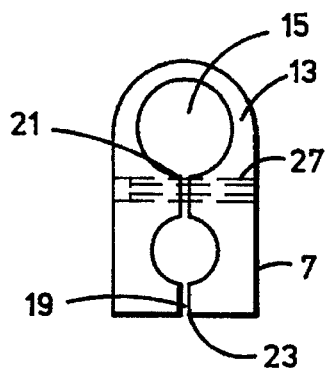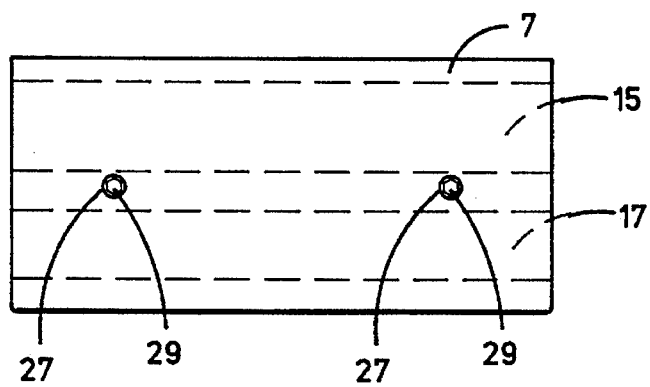
FIG. 9  FIG. 10
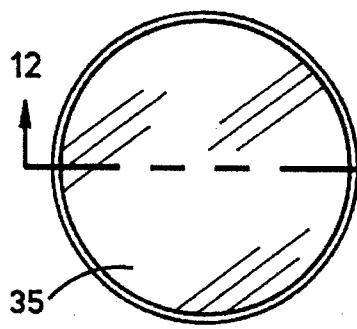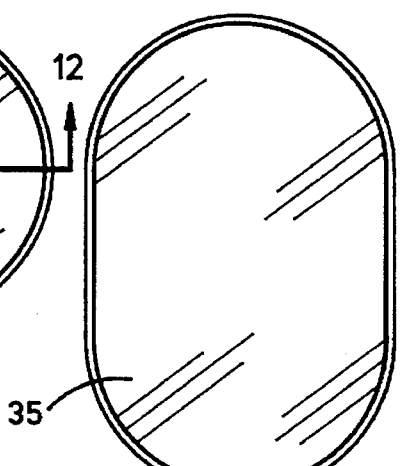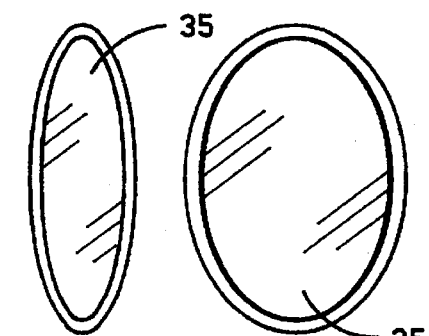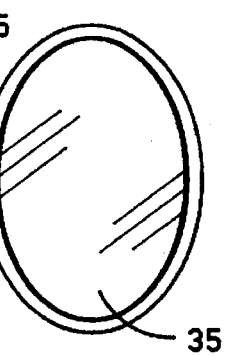
FIG. 11  FIG. 13  FIG. 14  FIG. 15
FIG. 12

PRECISION SIGHTING INSTRUMENT FOR VIEWING OBSTRUCTED AREAS

FIELD OF THE INVENTION

The present invention generally relates to a precision sighting instrument for concentrating light on the center of a pivotable mirror to enable accurate viewing of details in obstructed areas. More particularly it relates to a focusable light source integral to a compact configuration with a pivotable mirror, which enables sighting of the reflected area, especially for work involving details in dark recesses in mechanical and other equipment.

BACKGROUND

Space conservation is increasingly a premium factor in equipment design. Electronic technicians as well as machinery mechanics are recurrently confronted with troubleshooting problems in dark recesses and hard to reach places. The modern trend toward space economy in mechanical and electronic design presents ever increasing problems for the technician to view hard to reach potential problem areas without unnecessarily disassembling encasements and removing components. Accordingly, the ability to avoid displacement of functional components during technical operations provides significant damage risk control to equipment as well as means toward time management during assessment.

Technicians and mechanics in many contemporary situations in order to view otherwise obstructed areas are forced to use a light source as well as a separate hand-held mirror which in combination often tend to be awkward and may even require the use of both hands. The positioning of a conventional mirror in an obstructed region to reflect an area of interest to the viewer's line of sight is a task in itself. The added task of positioning a light source such that enough of the emitted light will be transmitted to a portion of the mirror to illuminate the desired location and coincide with the viewer's line of sight is difficult indeed. Moreover, diffuse light reflected from the surrounding area of the mirror tends to yield very poor contrast against the reflected area to be viewed.

Presently available lighted mirrors are generally constructed for wide-angle viewing. U.S. Pat. No. 5,428,484, issued Jun. 27, 1995 shows a hand held telescoping mirror device which includes a light bulb situated close to the mirror to provide a broad illumination region. U.S. Pat. No. 4,907,135, issued Mar. 6, 1990 shows a pen light having a removable conventional fixed-angle mirror. U.S. Pat. No. 2,107,791, issued Feb. 8, 1938 discloses a mirror with an attachable flashlight and a conical hood to direct the light to the fixed angle mirror. Other examples of this general type are shown in: U.S. Pat. No. 2,222,879, issued Nov. 26, 1940; U.S. Pat. No. 1,750,194, issued Mar. 11, 1930; and U.S. Pat. No. 1,656,754, issued Jan. 17, 1928.

Previous attempts to construct instruments to solve the problem have employed sources which disseminate light as well as mirrors in structural arrangements which have inherently lacked the functional precision to allow a user to focus on a selected area for accurately viewing details. The need clearly exists for a precision tool to enable exploring and accurately viewing obstructed areas and dark recesses for cost-effective maintenance of modern technical and mechanical equipment.

SUMMARY OF THE INVENTION

A precision sighting device is provided comprising a longitudinally extendable/retractable rigid rodlike member, a focusable light source mounted at one end of the rodlike member, longitudinally parallel and adjacent to the rodlike member, by at least one holding bracket such that light may be emitted from the focusable light source and directed lengthwise and parallel to the rodlike member toward an opposite end of the rodlike member, a tandem ball joint at the opposite end of the rodlike member formed in part by a first ball integral to the opposite end of the rodlike member, and a mirror pivotally connected by a flange extending from a peripheral portion of the mirror, to a second ball of said tandem ball joint—such that light emitted from the focusable light source may form a focal point or area on the center of the mirror at an exponential number of positions of the mirror with respect to focal lengths of light emitted from the focusable light source.

Accordingly, an object of this invention is to provide new and improved tool for viewing dark recesses as well as obstructed areas in general which are difficult to see with the naked eye. Here, an object is to provide a focusable high intensity light source integral to a compact structural design to consistently provide for optical convergence of light at a center point of an integral mirror at many different focal lengths from the light source and angular positions of the mirror with respect to the integral light source.

Another object of the invention is to provide an instrument which is especially suited for precision in aiming light and illuminating details very brightly for accurate and clear viewing while greatly reducing light reflected from the background of the area surrounding the mirror thereby providing much improved visual contrast.

A further object of the invention is to provide an instrument wherein a user is able to very precisely sight and focus light on an area by viewing along the top of the instrument, preferably along the bracket(s), to the center of the mirror as though sighting a gun.

Accordingly, various embodiments of the precision sighting instrument described herein are intended to provide significant advantages to viewing obstructed areas to the technician—and therefore equipment damage risk control as well as corollary assistance in time management. These and other objects of the invention will be readily apparent from the following detailed description and the accompanying drawings.

BRIEF DESCRIPTION OF THE DRAWINGS

The invention may take physical form in certain parts and arrangements of parts, preferred embodiments of which are described in this specification and some of which are illustrated in the accompanying drawings which form a part thereof and:

FIG. 1 is a side elevational partially sectioned view of a basic embodiment of a precision sighting instrument.

FIG. 2 is a bottom elevational view of a basic embodiment of the present invention.

FIG. 3 is a rear elevational view of a basic embodiment of a precision sighting instrument.

FIG. 4 is a front elevational view of a basic embodiment of a precision sighting instrument.

FIG. 5 is a frontal partially sectional view of a basic embodiment of a holding bracket.

FIG. 6 is a frontal partially sectional view of another basic embodiment of a holding bracket.

FIG. 7 is a frontal partially sectional view of another basic embodiment of a holding bracket.

FIG. 8 is a side partially sectional view of a basic embodiment of a holding bracket.

FIG. 9 is a frontal partially sectional view of another basic embodiment of a holding bracket.

FIG. 10 is a side partially sectional view of another basic embodiment of a holding bracket.

FIG. 11 is a frontal view of an of example round mirror for use in an embodiment of the present invention.

FIG. 12 is a cross-sectional side view of an example concave round mirror for use in an embodiment of the present invention.

FIG. 13 is a frontal view of an of example oblong mirror for use in an embodiment of the present invention.

FIG. 14 is a frontal view of an of example elliptical mirror for use in an embodiment of the present invention.

FIG. 15 is a frontal view of another example elliptical mirror for use in an embodiment of the present invention.

DETAILED DESCRIPTION OF PREFERRED EMBODIMENTS

A novel precision sighting instrument is disclosed herein which enables the accurate sighting of details in obstructed areas and dark recesses which are characteristic of technical equipment. Much of the functional problems involving viewing instruments have previously existed due to instruments lacking a focusable high intensity light source and an integral extendable structural design to provide for optical convergence of light at the center point of a pivotable mirror which is in alignment with the line of sight in a myriad of different positions. The present invention may optimally pinpoint or spotlight a selected area and thereby illuminate the details for accurate viewing.

"Obstructed areas" as used herein defines hard to reach dark recesses as well as areas in general which are difficult to view with the naked eye.

A basic embodiment of a precision sighting instrument which shows various features of the present invention is illustrated in FIG. 1 comprising a longitudinally extendable/retractable rigid rodlike member 1. In this particular embodiment the rodlike member 1 is a slidably telescoping structure shown in the retracted position. A focusable light source 3, cylindrical in this particular embodiment, is mounted at one end 5 of the rodlike member 1 longitudinally parallel and adjacent to the rodlike member 1 by at least one holding bracket 7 such that light 8 may be emitted from the focusable light source 3 and directed lengthwise and parallel to the rodlike member 1 toward an opposite end 9 of the rodlike member. A holding bracket 7, also particularly shown in FIG. 5, is comprised of a rigid rectangular box shape body 11. An upright longitudinal face of the body 13 having an upper bore 15 for passage therethrough of the focusable light source 3, and a lower bore 17 for passage therethrough of the rodlike member 1. The holding bracket 7 has a slit therethrough 19 the upright longitudinal face of the body 13 passing from a bottom of the upper bore 21 to a bottom of the body 23 to enable clamping action. An upright longitudinal side of the body 25, particularly shown in FIG. 8 and FIG. 10, having at least one bore 27 below a profile of the upper bore 15 for passage therethrough of a bolt 29. A tandem ball joint 31 is located at the opposite end 9 of the rodlike member 1 which is formed in part by a first ball 33 integral to the opposite end 9 of the rodlike member 1. A mirror 35 is pivotally connected by a flange 37 extending from a peripheral portion of the mirror 39 to a second ball 41 of the tandem ball joint 31. Light emitted 8 from the focusable light source 3 may form a focal point 43 on the center of the mirror 45 at an exponential number of positions of the mirror with respect to a focal length 32 or many different focal lengths of light emitted 8 from the focusable light source 3.

The longitudinally extendable/retractable rigid rodlike member 1 of the present invention allows for length adjustment 32 of the precision sighting instrument and thereby the distance position of the mirror 35 with respect to the focusable light source 3 and focal length 32 to optimally accommodate for different spatial and angular situations. The structural arrangement of the present invention, in particular the tandem ball joint 31 which allows the mirror 35 to be pivotally moved and lowered with respect to the rodlike member 1, in combination with the focusable light source 3, and 360° pivotable mirror 35, allows the user to converge emitted light 8 to the center of the mirror 45 at an exponential number of different angles, distances and positions of the mirror 35 with respect to the light source 3. The instrument described herein is especially suited to adjusting to an exponential number of focal lengths 32 to deliver a focal point 43 or area of light to the center of the mirror 45. The user is able to very precisely sight and focus light on an area by viewing along the top of the instrument, preferably along the bracket(s) 7, to the center of the mirror 45 as though sighting a gun. The instrument is especially useful for precision in aiming light and illuminating details very brightly for accurate and clear viewing.

In a preferred embodiment shown in FIG. 1 and FIG. 2 the rodlike member 1 is a cylindrical outer-shaped slidably telescoping integrally related rigid structure shown in the retracted position. In this embodiment, at least one section of the rodlike member is a rigid sleeve for the slidable insertion of at least one rigid, preferably solid, preferably non-rotating inner hexagonal rod. It is contemplated that a rodlike structure for use with the present invention may comprise several inner layers of extendable/retractable sleeve portions with the innermost being a solid rod. Most preferably the overall rodlike member is not separatable into different portions. Another contemplated embodiment of the longitudinally extendable/retractable rigid rodlike member 1 is comprised of two or more separatable sections which fit together similar to a multi-sectioned fishing rod.

The focusable light source 3 of the present invention allows for convergence of emitted light 8 at the center of the mirror 45 thus enabling the user to spotlight details in obstructed areas. The user may focus the light source, for instance by turning the head portion 4 of the twist-beam embodiment shown in FIG. 1, to provide different spotlights of various diameters within the mirror 35 to accommodate characteristic needs dictated by specific situations. A significant advantage of the present invention is the ability for the user to sight along the top of the instrument 7 to the center of the mirror 45 while adjusting the focusable light source 3, 4, to emit light 8 of a focal length 32 so that the breadth of the focal point is within the mirror, preferably at the center. This distinct advantage greatly reduces light reflected from the background of the area surrounding the mirror 35 thereby providing much improved visual contrast, e.g. black background, for viewing. Moreover, the intensification of light accomplished by the convergence of light emitted 8 on a central area of the mirror 45 provides for excellent illumination of details in the obstructed area to be viewed.

The focusable light source 3 is preferably of cylindrical shape as shown in FIG. 1. Other embodiments may have many different shapes; oval or hexagonal cross sections inter alia are contemplated embodiments of the focusable light source for use in the present invention. The focusable light source may employ a standard filament light bulb, although specialty high-intensity bulbs such as halogen, xenon, and krypton inter alia are preferred. Lenses for light focus of the highest quality are also preferred. Many other focusable light sources may be used without departing from the scope of the present invention including powerful light sources which require alternating current and therefore exterior power source.

The focusable light source 3 is mounted at one end 5 of the rodlike member 1 longitudinally parallel and adjacent to the rodlike member 1, preferably centered, by at least one holding bracket 7 such that light 8 may be emitted from the focusable light source 3 and directed lengthwise and parallel to the rodlike member 1 toward the opposite end 9 of the rodlike member. A preferred embodiment of the holding bracket 7, also particularly shown in FIG. 5, is comprised of a rigid rectangular box shape body 11. An upright longitudinal face of the body 13 having an upper bore 15 for passage therethrough of the focusable light source 3, and a lower bore 17 for passage therethrough of the rodlike member 1. The preferred holding bracket 7 has a slit therethrough 19 the upright longitudinal face of the body 13 passing from a bottom of the upper bore 21 to a bottom of the body 23 to enable clamping action. An upright longitudinal side of the body 25, particularly shown in FIG. 8 and FIG. 10, having at least one bore 27 below a profile of the upper bore 15 for passage therethrough of a bolt 29. Bolt as used herein is a general term referring to threaded screws, nonthreaded shafts, bolts for use with nuts, and general means for connection or attachment. The bore 27 for passage of the bolt 29 is preferably threaded and has a slightly a recessed portion for use of a threaded bolt having a sockethead cap screw or head for a screwdriver or alan wrench. Any holding bracket may be used with the present invention. The invention may employ one or more holding brackets. Holding brackets especially suited for use with the present invention are shown in FIG. 5, FIG. 6, FIG. 7, FIG. 8, FIG. 9, and FIG. 10. The mounting bracket shown in FIG. 6, wherein the upright longitudinal face of the body has an arched top width, with the side view shown in FIG. 8, is most preferred to be used as a pair—as shown in FIG. 1 and FIG. 2. Another embodiment of a mounting bracket is to be used as a pair is shown in FIG. 7, wherein the upright longitudinal face of the body has an arched top width and an arched bottom width, with the side view shown in FIG. 8. An embodiment of the present invention wherein one holding bracket may be used is exemplified with an elongated version of a holding bracket shown in FIG. 9, with the side view shown in FIG. 10, having two separate bores 27 below a profile of the upper bore 15 for passage therethrough of two separate bolts 29.

As shown in FIG. 1, FIG. 2, and FIG. 4, a tandem ball joint of the precision sighting instrument 31 is located at the opposite end 9 of the rodlike member 1—formed by a first ball 33 integral to the opposite end 9 of the rodlike member 1, and a second ball 41 connected by a flange 37 to the peripheral or back portion of a mirror 39. A preferred embodiment of the tandem ball joint 31 (as shown) is formed by the first 33 and second 41 balls clamped between two, generally flat, oblong plates 34, each plate having two semihemispherical sockets 36 for receiving a semi hemisphere of each of the first and second balls and a central bore 38 located at a flat portion between the sockets for passage therethrough of a bolt 40 to hold the plates 34 together against the bails. The tandem ball joint 31 of the present invention is subject to many different variations and may be constructed as is otherwise known to those of ordinary skill in the mechanical arts. The tandem ball joint of the present invention may also be substituted in similar construction with other ball joints comprised of one to five balls. Light emitted 8 from the focusable light source 3 may form a focal point area 43 on the center of the mirror 45 at an exponential number of positions of the mirror with respect to the light source 3 or many different focal lengths of light emitted 8 from the focusable light source 3.

The mirror of the precision sighting instrument is preferably round—and, as shown in FIG. 11, most preferably circular. Other preferred embodiments of the present invention are comprised of circular concave mirrors FIG. 12 for magnification, oblong mirrors (one example of which is shown in FIG. 13), and elliptical mirrors (examples of which are shown in FIG. 14 and FIG. 15). Still other embodiments may employ various other shapes without departing from the scope of the invention including, but not limited to triangular, square, rectangular, or polygonal mirrors.

The precision sighting instrument described herein arranged in a compact configuration is especially suited for accurate viewing of details in obstructed areas, especially for work involving details in dark recesses in mechanical and other equipment. It is an object of the present invention to provide optical convergence of light is at the center point of a mirror which may be placed at manifold different angular positions in alignment with the line of sight to accurately focus on particular details of a reflected area. Electronic technicians as well as machinery mechanics may use the precision sighting instrument to troubleshoot problems in dark recesses and hard to reach places—and focus on details for examination—without unnecessarily disassembling encasements and removing components. Accordingly, various embodiments of the precision sighting instrument described herein are intended to provide significant advantage to the technician in damage risk control as well as corollary assistance in time management.

The precision sighting instrument described herein is designed and intended for use in and around computers and electrical equipment in addition to its intended use for troubleshooting in and around mechanical equipment. Therefore for safety reasons components of the present invention may be constructed from rigid non-conducting polymeric and monomer materials such as lucite, plastic, and fiberglass. Preferred embodiments of the present invention are constructed from lucite, rigid metals and metal alloys such as anodized aluminum, stainless steel, tempered steel, and brass alloys. Embodiments of the present invention which are constructed of conducting material may be insulated from electrical conduction by encasement by at least one layer of non-conducting material such as rubber, plastic, vinyl, nylon and/or polyamide. Other preferred materials for construction of the instrument as well as the additional members include ultra high molecular weight polyethylene, titanium alloys, chromium cobalt alloys, tantalum, Vitallium ®, aluminum oxide, and molybdenum alloys. Any sufficiently rigid compatible material that can be fashioned to fit the physical characteristics described herein may be used to construct the precision sighting instrument.

A preferred embodiment of the present invention is constructed using a twist-beam krypton focusable light source having a cam action focusable beam and aircraft-grade anodized aluminum alloy body, 6061-T651 anodized aluminum alloy brackets, and a tempered spring steel rodlike member/tandem ball joint/mirror. Another preferred embodiment employs a MINI-MAG focusable light source (Mag Instruments, Ontario, Calif.) and an ULLMAN DEVICES C-2 telescopic inspection mirror. Various high quality custom mirrors and constituents for use as integral components of the present invention are available, for instance, from ULLMAN DEVICES (Ridgefield, Conn.) and McMASTER-CARR (Los Angeles, Calif.).

The following example is provided by way of illustration and are not included for the purpose of limiting the invention.

EXAMPLE

I Construction of Brackets

Cut lengths of 6061-T651 aluminum alloy stock to a slightly oversized desired length of the final bracket upright longitudinal face. Machine one end of the blank square—all other desired dimensions are referenced from this cut. Drill a lower bore for passage therethrough of the rodlike member centered near the machined end. Drill an aligned and centered upper bore for passage therethrough of the focusable light source. Deburr both sides of the holes. Drill a countersink hole to accept a socket head cap screw in the upright longitudinal side of the body below a profile of the upper bore. Drill another hole from the bottom of the counter-sink hole more than halfway through the body to allow a threaded portion of a socket head cap screw to pass through half the body. Drill a tap-hole for a screw thread to pass through the remaining portion of the body. Tap the screw thread. The body is then mounted on a rotary table by means of the upper bore for passage therethrough of the focusable light source. Radius the top of the upright longitudinal face to yield an arched top width. Deburr the radius. Using a slitting saw cut a slit therethrough the upright longitudinal face of the body from the bottom center of the body to a bottom of the upper bore for a pinch-bolt to enable clamping action. Tumble the machined products in deburring media to remove all burrs and tool marks for 30 hours—cleaning or replacing the media every four hours. Tumble the machined products in polish media to a shiny finish. Anodize the products for a protective coating. Assemble the brackets using a small wedge in the slit to slightly open the saw cut, slide the bracket over the focusable light source and the rodlike member through the upper bore and lower bore, respectively. Tighten the socket head cap screw through the upright longitudinal side of the body below a profile of the upper bore to maintain precise alignment of the focusable light source and the rigid rodlike member.

Changes modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the precision sighting instrument which are obvious to those skilled in mechanical arts and optics or related fields are intended to be within the scope of the following claims.

What is claimed is:

1. A precision sighting instrument for viewing obstructed areas, which comprises:

a longitudinally extendable/retractable rigid rodlike member, a focusable light source mounted at one end of the rodlike member, longitudinally parallel and adjacent to the rodlike member by at least one holding bracket such that light may be emitted from the focusable light source and directed lengthwise and parallel to the rodlike member toward an opposite end of the rodlike member, a tandem ball joint at said opposite end of the rodlike member formed in part by a first ball integral to said opposite end of the rodlike member, and a mirror pivotally connected by a flange extending from a peripheral portion of the mirror, to a second ball of said tandem ball joint—such that light emitted from the focusable light source may form a focal point on the center of the mirror at an exponential number of positions of the mirror with respect to a focal length of light emitted from the focusable light source.

2. A precision sighting instrument for viewing obstructed areas according to claim 1 wherein the focusable light source is cylindrical and is mounted by two holding brackets.

3. A precision sighting instrument for viewing obstructed areas according to claim 1 wherein the longitudinally extendable/retractable rigid rodlike member is slidably telescoping.

4. A precision sighting instrument for viewing obstructed areas according to claim 1 wherein the tandem ball joint is formed by the first and second balls clamped between two generally flat oblong plates, each plate having two semi-hemispherical sockets for receiving a semi hemisphere of each of the first and second balls and a central bore located at a flat portion between the sockets for passage therethrough of a bolt to hold the plates together against the balls.

5. A precision sighting instrument for viewing obstructed areas according to claim 1 wherein the mirror is round.

6. A precision sighting instrument for viewing obstructed areas according to claim 5 wherein the mirror is concave.

7. A precision sighting instrument for viewing obstructed areas according to claim 1 wherein the mirror is oblong.

8. A precision sighting instrument for viewing obstructed areas according to claim 1 wherein the mirror is elliptical.

9. A holding bracket for use with the precision sighting instrument according to claim 1 comprising:

a rigid rectangular box shape body, an upright longitudinal face of the body having an upper bore for passage therethrough of the focusable light source, and a lower bore for passage therethrough of the rodlike member, a slit therethrough the upright longitudinal face of the body passing from a bottom of the upper bore to a bottom of the body to enable clamping action, and an upright longitudinal side of the body having at least one bore below a profile of the upper bore for passage therethrough of a bolt.

10. A holding bracket according to claim 9 wherein:

the upright longitudinal face of the body has an arched top width.

11. A holding bracket according to claim 10 wherein:

the upright longitudinal face of the body has an arched bottom width.

12. A precision sighting instrument for viewing obstructed areas, which comprises:

a longitudinally extendable/retractable rigid rodlike member, a focusable light source mounted at one end of the rodlike member, longitudinally parallel and adjacent to the rodlike member by at least one holding bracket such that light may be emitted from the focusable light source and directed lengthwise and parallel to the rodlike member toward an opposite end of the rodlike member, wherein said holding bracket is comprised of a rigid rectangular box shape body, an upright longitudinal face of the body having an upper bore for passage therethrough of the focusable light source, and a lower bore for passage therethrough of the rodlike member, a slit therethrough the upright longitudinal face of the body passing from a bottom of the upper bore to a bottom of the body to enable clamping action, and an upright longitudinal side of the body having at least one bore below a profile of the upper bore for passage therethrough of a bolt, and a tandem ball joint at said opposite end of the rodlike member formed in part by a first ball integral to said opposite end of the rodlike member, and a mirror pivotally connected by a flange extending from a peripheral portion of the mirror, to a second ball of said tandem ball joint—such that light emitted from the focusable light source may form a focal point on the center of the mirror at an exponential number of positions of the mirror with respect to a focal length of light emitted from the focusable light source.

13. A precision sighting instrument for viewing obstructed areas according to claim 12 wherein the upright longitudinal face of the body of the holding bracket has an arched top width.

14. A precision sighting instrument for viewing obstructed areas according to claim 13 wherein the focusable light source is cylindrical and is mounted by two holding brackets.

15. A precision sighting instrument for viewing obstructed areas according to claim 12 wherein the longitudinally extendable/rigid rodlike member is slidably telescoping.

16. A precision sighting instrument for viewing obstructed areas according to claim 12 wherein the tandem ball joint is formed by the first and second balls clamped between two generally flat oblong plates, each plate having two semi-hemispherical sockets for receiving a semi hemisphere of each of the first and second balls and a central bore located at a flat portion between the sockets for passage therethrough of a bolt to hold the plates together against the balls.

17. A precision sighting instrument for viewing obstructed areas according to claim 12 wherein the mirror is round.

18. A precision sighting instrument for viewing obstructed areas according to claim 17 wherein the mirror is concave.

19. A precision sighting instrument for viewing obstructed areas according to claim 12 wherein the mirror is oblong.

20. A precision sighting instrument for viewing obstructed areas according to claim 12 wherein the mirror is elliptical.

* * * * *